US00PP25506P3

(12) United States Plant Patent
Danziger

(10) Patent No.: US PP25,506 P3
(45) Date of Patent: May 5, 2015

(54) ***LANTANA* PLANT NAMED 'DANTAN30'**

(50) Latin Name: *Lantana camara*
Varietal Denomination: DANTAN30

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/986,312

(22) Filed: Apr. 18, 2013

(65) Prior Publication Data

US 2014/0317800 P1 Oct. 23, 2014

(51) Int. Cl.
*A01H 5/00* (2006.01)

(52) U.S. Cl.
USPC ..... Plt./227

(58) Field of Classification Search
CPC ..... A01H 5/00; A01H 5/02
USPC ..... Plt./227
See application file for complete search history.

*Primary Examiner* — Susan McCormick Ewoldt
*Assistant Examiner* — Keith Robinson
(74) *Attorney, Agent, or Firm* — Cassandra Bright

(57) ABSTRACT

A new and distinct *Lantana* cultivar named 'DANTAN30' is disclosed, characterized by lack of seed production. Inflorescences distinctively change color from yellow to orange to red. The new variety has a semi trailing and spreading habit and small rounded leaves. The new variety is a *Lantana*, normally produced as an outdoor garden or container plant.

2 Drawing Sheets

Figure 1:
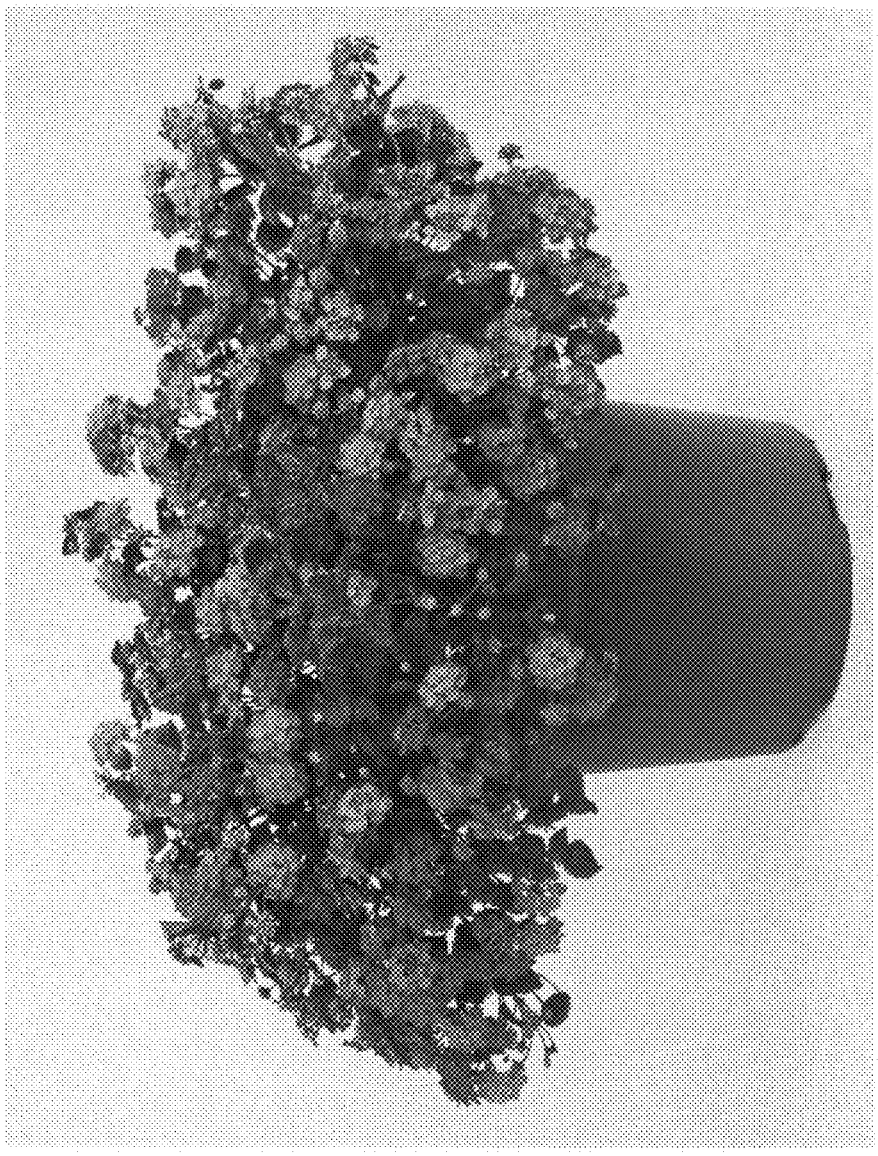

Latin name of the genus and species: *Lantana camara.*
Variety denomination: 'DANTAN30'.

BACKGROUND OF THE INVENTION

The new *Lantana* cultivar is a product of a planned breeding program conducted by the inventor, Gavriel Danziger, in Moshav Mishmar Hashiva, Israel. The objective of the breeding program was to produce new *Lantana* varieties for ornamental commercial applications. The open pollination resulting in this new variety was made during March of 2007.

The new variety originated as a seedling from the open pollination of various, *Lantana* varieties. The actual seed parent is unknown as seed was bulk harvested from the collection of *Lantana* plants. The open pollination resulting in the bulk collected seed was organized by the inventor in an open field at a research nursery in Moshav Mishmar Hashiva, Israel. The new variety was selected in August of 2008.

Asexual reproduction of the new cultivar has been performed by vegetative cuttings. This was first performed at a research greenhouse in Moshav Mishmar Hashiva, Israel in August of 2008 and has shown that the unique features of this cultivar are stable and reproduced true to type in numerous successive generations.

SUMMARY OF THE INVENTION

The cultivar 'DANTAN30' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANTAN30' These characteristics in combination distinguish 'DANTAN30' as a new and distinct *Lantana* cultivar:

1. Semi trailing and spreading plant habit.
2. Small rounded leaves.
3. No seed or fruit set.
4. Inflorescence changes color from yellow to orange and ultimately to red.

COMMERCIAL COMPARISON

Plants of the new cultivar 'DANTAN30' are comparable to the variety *Lantana* 'Bandana Cherry Surprise', unpatented. The two *Lantana* varieties are similar in most horticultural characteristics; however, the new variety 'DANTAN30' produces small round leaves compared to the large and wide leaves of 'Bandana Cherry Surprise'. Additionally plants of 'DANTAN30' exhibit a change of inflorescence color from yellow to orange and finally to red whereas the comparator 'Bandana Cherry Surprise' inflorescence changes from yellow to pink. Finally 'DANTAN30' has a more spreading habit compared to the compact and mounded habit of comparator 'Bandana Cherry Surprise'.

Plants of the new cultivar 'DANTAN30' are comparable to the variety *Lantana* 'Bandana Peach', unpatented. The two *Lantana* varieties are similar in most horticultural characteristics; however, the new variety 'DANTAN30' produces small round leaves compared to the large and wide leaves of 'Bandana Peach'. Additionally 'DANTAN30' change of inflorescence is from yellow to orange and finally to red whereas the comparator 'Bandana Peach' inflorescence changes from yellow to peach colored. Finally 'DANTAN30' has a more spreading habit compared to the compact and mounded habit of comparator 'Bandana Peach'.

BRIEF DESCRIPTION OF THE PHOTOGRAPHS

The accompanying photograph in FIG. 1 illustrates in full color a typical plant of 'DANTAN30' grown in a greenhouse, in a 12 cm pot. Age of the plant photographed is approximately 8 weeks from a rooted cutting.

Figure 2:
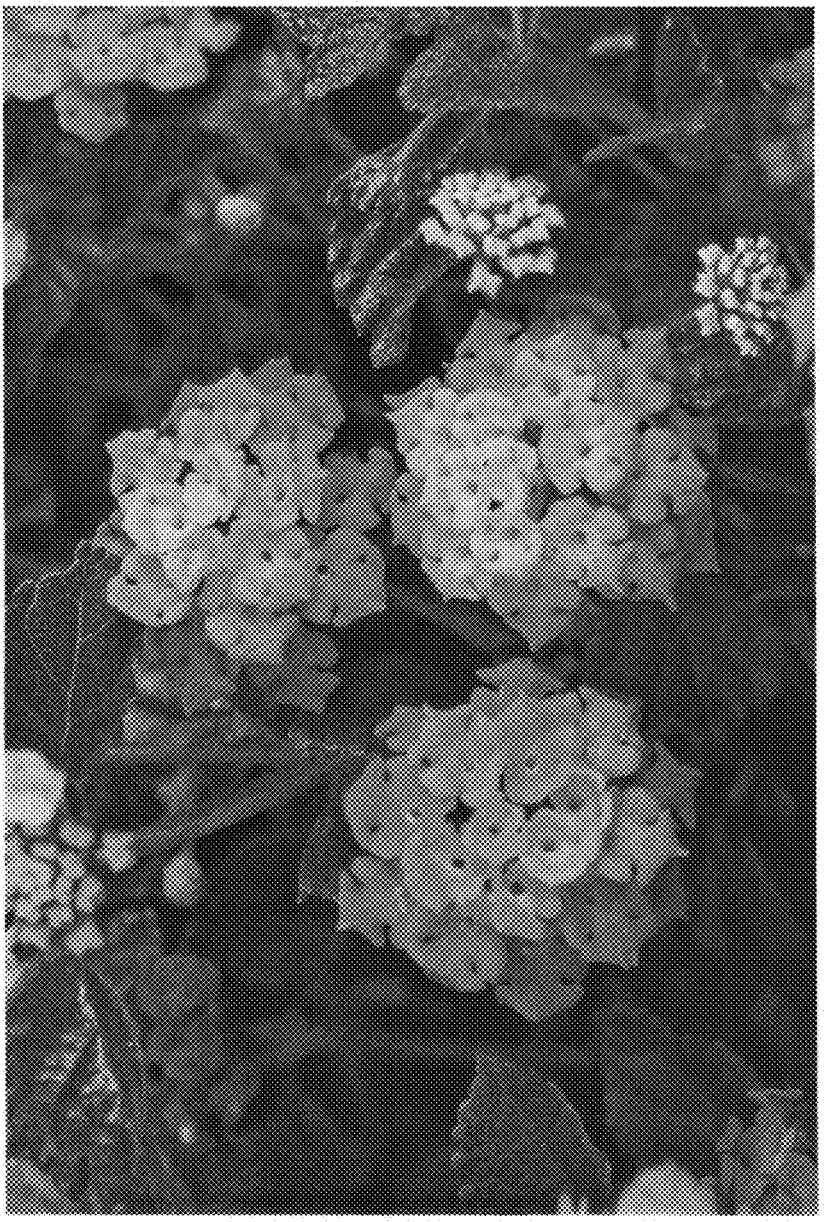

FIG. 2 illustrates in full color a close up of a typical bloom of 'DANTAN30'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DANTAN30' plants grown in a greenhouse, in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types.

Botanical classification: *Lantana camara* 'DANTAN30'.

PROPAGATION

Time to initiate roots: About 5 to 6 days.

Root description: Fleshy and branching.

PLANT:

Age of plant described: Approximately 12 weeks from a rooted cutting.

Pot size of plant described: 12 cm.

Growth habit: Semi trailing and spreading to the sides a little.

Height: 20-25 cm.

Plant spread: 30-35 cm.

Growth rate: Moderate.

Branching characteristics: Well branched, basal branching.

Length of primary lateral branches: 30 cm.

Diameter of lateral branches: 0.3-0.5 cm.

Quantity of primary lateral branches: 4-6.

Characteristics of primary lateral branches:

- *Form*.—Straight, slightly ribbed longwise.
- *Diameter*.—0.5-0.7 cm.
- *Color*.—The side that face the sun light is yellow-green group 148A RHS the side that does not face the sun light is yellow group 144A RHS.
- *Texture*.—Stiff, with very light and delicate hair.
- *Strength*.—Moderately strong.

Internode length: 3-4 cm.

FOLIAGE:

Leaf:

- *Arrangement*.—Opposite.
- *Quantity*.—Approximately 30-40 per branch.
- *Average length*.—3 cm.
- *Average width*.—2 cm.
- *Shape of blade*.—Oval.
- *Apex*.—Moderately acute.
- *Base*.—Pointed.
- *Margin*.—Crenate.
- *Texture of top surface*.—Coarse, with tiny rough hairs.
- *Texture of bottom surface*.—Somewhat less pubescent than the upper surface.
- *Aspect*.—Mainly flat foliage, attached at 45 degree and from the lateral branch.
- *Color*.—Young foliage upper side: Green group 137A RHS. Young foliage under side: Green group 137B RHS. Mature foliage upper side: Yellow-green group 139A RHS. Mature foliage under side: Yellow-green group 147A RHS. Venation: Midrib with secondary veins and very dense tertiary veins across. Type: Anastomosing. Venation color upper side: Yellow-green group 147C RHS. Venation color under side: Yellow-green group 147B RHS.

Petiole:

- *Length*.—0.5 cm.
- *Diameter*.—0.2 cm.
- *Color*.—Yellow green group 144A RHS.
- *Texture*.—Pubescent, with short soft hair.

FLOWER

Natural flowering season: Spring to Fall.

Days to flowering from rooted cutting: 8 weeks.

Inflorescence and flower type and habit: Umbel.

Individual flower shape: Trumpet shaped.

Rate of flower opening: 4 to 6 days from bud to fully opened flower.

Flower longevity on plant: 1-1.5 weeks (depending on outdoor temperature, higher temperatures result in shorter flower longevity).

Persistent or self-cleaning: Self cleaning.

Overall inflorescence size:

- *Height*.—Approximately 2-3 cm.
- *Diameter*.—Approximately 3 cm.

Individual flower size:

- *Height*.—Approximately 1.5 cm.
- *Diameter*.—Approximately 0.5-0.8 cm.

Bud:

- *Shape*.—Tubular.
- *Length*.—0.8 cm.
- *Diameter*.—0.3 cm.
- *Color*.—Yellow group 13A close to the base. Orange-red group 33A at the tip.

Corolla:

- *Petals/lobes*.—Number: 4 lobes fused together forming a radial shape. Length: Upper and lower lobes 0.4 cm. Right and left lobes 0.3 cm. Width: Upper and lower lobes 0.7 cm. Right and left lobes 0.3 cm.
- *Shape*.—Single-rounded. Aspect: Erect from the base of the inflorescence. Margin: Entire. Texture: Smooth.

Color:

- *When opening*.—Upper surface: Yellow-orange group 23A RHS. Lower surface: Yellow-orange group 21B RHS.
- *Fully opened*.—Upper surface: Red group 42A RHS. Lower surface: Orange-red group 34B RHS.
- *Throat/tube*.—Color: Yellow-orange group 18A RHS. Texture: Pubescent, covered with tiny dense smooth hair resembling silk.

Calyx/sepals:

- *Form*.—2 oblong bracts fuse together, forming a tubular shape. Base fused, apex acute.
- *Length*.—0.4 cm.
- *Diameter*.—0.2 cm.
- *Sepal shape*.—Strap shaped.
- *Sepal margin*.—Entire.
- *Sepal texture*.—Smooth, covered with tiny dense smooth hair.
- *Sepal color*.—(transparent) Yellow green group 144B RHS.

Flower bracts/inflorescence bracts:

*Arrangement*.—Solitary, single occurring under each flower within the inflorescence.

*Length*.—Approximately 0.6 cm.

*Width*.—Approximately 0.1 cm.

*Shape*.—Strap shaped.

*Apex*.—Sharply pointed.

*Margin*.—Entire.

*Texture*.—Delicate pubescent, smooth, resembling silk.

*Color*.—Upper surface: Yellow green group N146D RHS close to the base and yellow-green group N146B RHS at the tip. Lower surface: Yellow green group N146D close to the base and yellow-green group N146C RHS at the tip.

Peduncles:

*Length*.—Approximately 4-5 cm.

*Diameter*.—Approximately 0.2 cm.

*Angle*.—about 45 degrees.

*Strength*.—Medium.

*Texture*.—Smooth, covered with tiny dense smooth hair — resembling silk.

*Color*.—Yellow-green group 144A RHS.

*Flower fragrance*.—Lemon-like.

Pedicels:

*Length*.—Approximately 0.2 cm.

*Diameter*.—Approximately 0.1 cm.

*Angle*.—About 35 degrees.

*Strength*.—Moderate.

*Texture*.—Slightly pubescent.

*Color*.—Yellow-green group 144A RHS.

REPRODUCTIVE ORGANS

Stamens:

*Number* (*per flower*).—4.

*Filament length*.—0.05 cm.

*Anthers*.—Shape: Obovate. Length: 0.1 cm. Width: 0.1 cm. Color: Young: Yellow group 2A RHS. Mature: Grey-brown group N199A RHS.

Pollen:

*Amount*.—None.

Pistils:

*Quantity per flower*.—1.

*Length*.—0.2 cm.

*Stigma*.—

*Length*.—Approximately 0.05 cm.

*Diameter*.—Approximately 0.05 cm.

*Color*.—Green-yellow group 1B RHS.

*Ovary color*.—Green group 143B RHS.

*Stigma*.—Yellow-green N144C RHS.

*Shape*.—Ball shaped.

*Color*.—Yellow-green group 149B RHS.

OTHER CHARACTERISTICS

Seeds and fruits: None.

Disease/pest resistance: Neither resistance nor susceptibility to common diseases and pests of *Lantana* has been observed.

Temperature tolerance: Can tolerate high temperature and drought.

What is claimed is:

1. A new and distinct cultivar of *Lantana* plant named 'DANTAN30' as herein illustrated and described.

* * * * *